United States Patent [19]
Kittelsen et al.

[11] Patent Number: 5,385,155
[45] Date of Patent: Jan. 31, 1995

[54] MOUTHGUARD SIZING KIT

[75] Inventors: Jon D. Kittelsen, Fridley; Paul C. Belvedere, Edina; Anne M. Kittelsen, Roseville, all of Minn.

[73] Assignee: E-Z Gard Industries, Inc., Minneapolis, Minn.

[21] Appl. No.: 127,759

[22] Filed: Sep. 28, 1993

[51] Int. Cl.⁶ .................................. A61C 5/14
[52] U.S. Cl. ............................ 128/861; 128/859
[58] Field of Search .................... 128/859–861, 128/62 A; 2/2; 433/6, 214, 37

[56] References Cited

U.S. PATENT DOCUMENTS

| | | | |
|---|---|---|---|
| 2,933,811 | 4/1960 | Lifton | 433/37 |
| 3,416,527 | 12/1968 | Hoef | 128/862 |
| 3,916,527 | 11/1975 | Linkow | 433/37 |
| 4,063,552 | 12/1977 | Going | 128/861 |
| 4,763,791 | 8/1988 | Halverson | 433/37 |
| 4,848,365 | 7/1989 | Guarlotti | 128/861 |
| 5,031,611 | 7/1991 | Moles | 433/6 |
| 5,154,609 | 10/1992 | George | 433/214 |

Primary Examiner—Michael A. Brown
Attorney, Agent, or Firm—Palmatier, Sjoquist & Helget

[57] ABSTRACT

A mouthguard sizing kit includes a dentition impression plate for placement into the mouth to receive a dentition imprint when forced against the upper dentition suitably by the lower jaw. A mouthguard sizing device is provided which indicates small to large mouthguards for comparison with the dentition imprint on the dentition impression plate for selection of the correctly sized small to large mouthguard for the user.

15 Claims, 2 Drawing Sheets

MOUTHGUARD SIZING KIT

BACKGROUND OF THE INVENTION

The present invention generally relates to a protective mouthguard for use in athletics and more particularly to a mouthguard sizing kit to permit the correct choice of size of mouthguard for proper fit by both the inexperienced user and the health care professional.

A number of mouthguards currently exist in the art for protecting the teeth, gums, tongue and lips and for further reducing the chance of shock, concussion or other injury as a result of high impact collisions and blows during athletic competition. In general, mouthguards existing in the art can be placed in two broad categories: tethered and untethered.

Untethered mouthguards are commonly fabricated by the user applying the boil-and-bite methodology or by dentists who fit the mouthguard to the exact contour of the user's teeth. These mouthguards are manufactured in a single configuration required trimming to their correct size with a scissors to insure correct size prior to fitting. After fitting, additional trimming may be necessary to assist in the comfortable fitting of the mouthguard with respect to the contour of the user's teeth, mouth and gums.

In certain athletic activities, which utilize a helmet or other protective headgear, and particularly in high impact sports such as football and hockey, it is desirable for the mouth piece to be tethered to the helmet, headgear, face mask or about the user's neck. The principal reasons are twofold. First, having the mouthguard tethered to the helmet or face mask eliminates the chance that the mouthguard will be lost or misplaced. Secondly and perhaps most importantly, a number of instances have occurred where the user inadvertently swallows the mouthguard which perhaps may not be properly fit and as a result of impact or otherwise during physical activity. This can result in the user choking on the mouth piece, thus causing severe injury or death.

It is also well known that the sizes of the mouthguard user's mouth, teeth, jaw and gums varies greatly from children to large adults, particularly the football players that typically play on the offensive line. Consequently, it has become necessary to offer boil-and-bite mouthguards in a variety of sizes ranging generally from small, medium to large. However, the individual wearer does not readily comprehend which particular size is appropriate for his or her mouth and runs the risk of purchasing and fitting an improperly sized mouthguard. An improperly sized mouthguard leads to discomfort and possible TMJ problems. Full mouthguard protection may also be minimized.

There is a need for a mouthguard sizing kit for use by the inexperienced and healthcare professionals that will assist in fitting the typical boil-and-bite or dentist fit mouthguard. Such a kit should allow for correct mouthguard sizing, to be simple and uncomplicated, safe and not reusable, easy to use and thereby permit the mouthguard user to avoid trying various mouthguard sizes.

SUMMARY OF THE INVENTION

A mouthguard sizing kit comprises a dentition impression plate for placement into the mouth to receive a dentition imprint when forced against the upper dentition suitably by the lower jaw. A mouthguard sizing means is provided which indicates small to large mouthguards for comparison with the dentition imprint on the dentition impression plate for selection of the correctly sized small to large mouthguard for the user.

A principal object and advantage of the present invention is that it allows for the correct size selection of mouthguards by the inexperienced and the experienced healthcare provider to assure proper and comfortable fitting of the appropriately sized mouthguard.

Another object and advantage of the present invention is that the kit is simple and easy to use, unlike complicated devices for oral or dentition impressions.

Another object and advantage of the present invention is that the mouthguard sizing kit is not reusable thereby preventing the spreading of germs from one potential mouthguard wearer to another.

Another object and advantage of the present invention is that the mouthguard sizing kit permits the avoidance of the prospective mouthguard wearer from trying various mouthguard sizes which will require sanitation of the undesirable mouthguards before others may attempt to fit the previously tried on mouthguard.

Another object and advantage is that the present invention will assure that the mouthguard wearer has the appropriately sized mouthguard for maximum protection, comfortable wear and TMJ protection.

Other objects and advantages will become readily apparent upon a reading and studying of the following specification, appended claims and attached figures.

DETAILED SPECIFICATION

Figure 1:
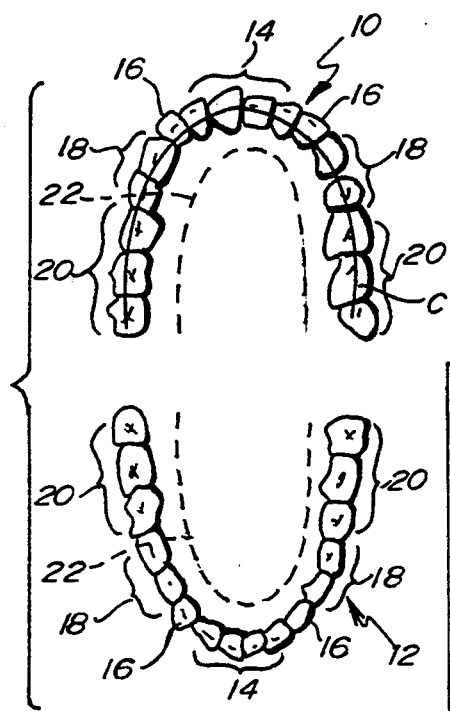
FIG. 1 is a plan view of the upper and lower dentitions of the mouth.

The present invention may be generally seen in FIGS. 3 through 9. The mouthguard sizing kit 39 generally comprises a mouthguard sizing means 40 and a dentition impression plate 44 which will permit the receipt of a dentition imprint 56 for comparison of the impression plate 44 with the sizing chart 42 of the mouthguard sizing means 40.

Referring specifically to FIG. 1, the upper and lower dentitions 10 and 12 of a person are shown. The teeth of an individual or person include incisors 14, canine or eye teeth 16, bicuspids 18 and molars 20. The dentition 10 or 12 generally extends from one molar 20 side around the bicuspids 18, canines 16, incisors 14 and molars 20 of the other molar side generally shown as a C for circumference.

Figure 2:
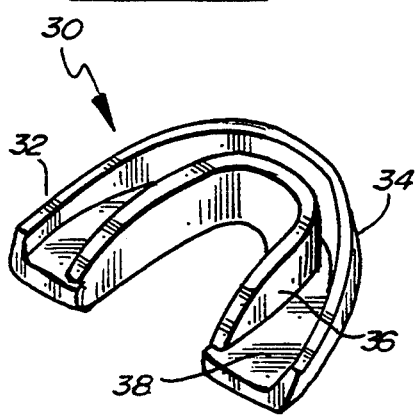
FIG. 2 is a perspective view of a mouthguard.

Referring to FIG. 2, a prior art mouthguard includes a mouth piece portion 32 having a forward or outer protective flange 34 and a rearward or inner protective flange 36 connected by a protective web or channel 38. It is well known that persons' mouths, teeth and jaws vary considerably in size from children to large adults. Consequently it is imperative that the correct size (small to extra large) be selected for the appropriate mouthguard 30 fitting to the wearer. After the appropriately sized mouthguard 30 is selected, the mouthguard generally may be softened by momentary placement in boiling water afterwhich it is fit and vacuumed against the teeth and gums of the wearer. Mouthguards are also commonly made of EVA (Ethylene Vinyl Acetate) material.

Figure 3:
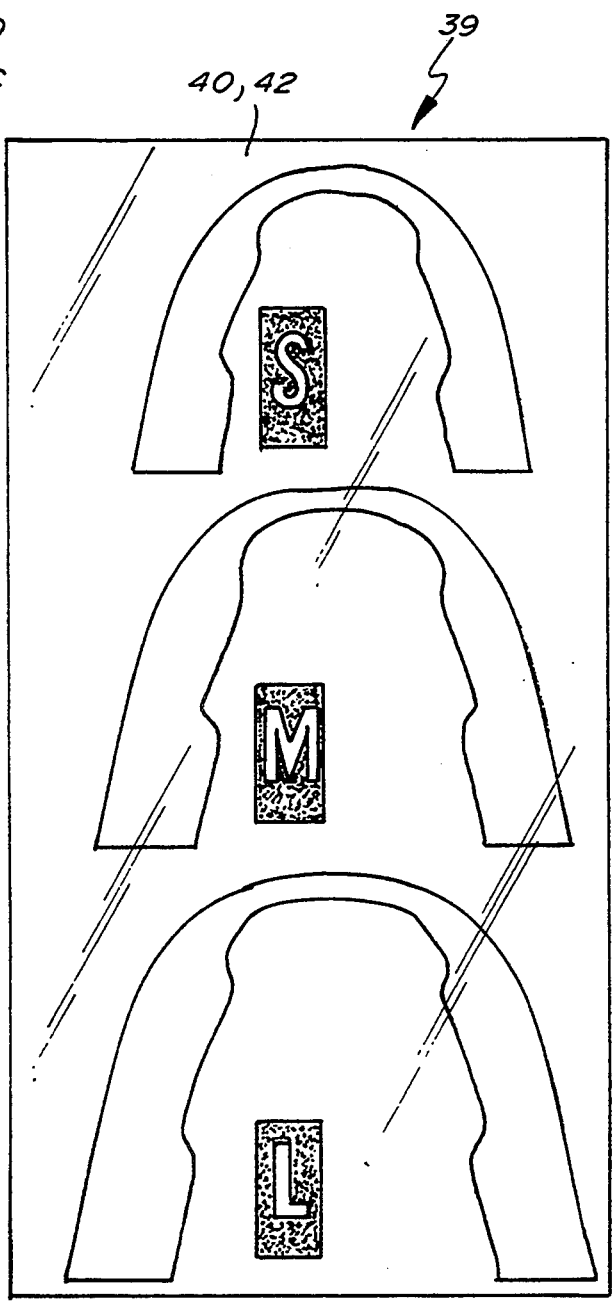
FIG. 3 is an actual size top plan view of a mouthguard sizing chart.

Referring to FIG. 3, the mouthguard sizing means 40 takes the form of a sizing chart 42. However, the sizing means 40 may simply be various sized mouthguards 30. Mouthguards 30 generally range from Small, Medium to Large. The sizing chart 42 is a simple and inexpensive way to show the actual true-to-life sizes of Small, Medium and Large mouthguards 30. The chart 42 may be translucent for easy comparison of the impressions plate 44 placed therebelow as appreciated below.

Figure 4:
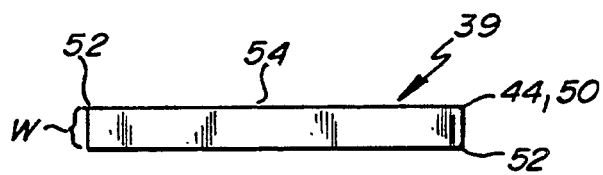
FIG. 4 is a top plan view of the elongate sizing strip.
Figure 5:
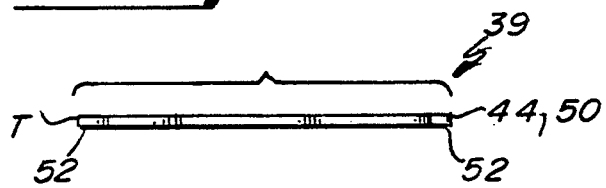
FIG. 5 is a side elevational view of the elongate sizing strip.
Figure 6:
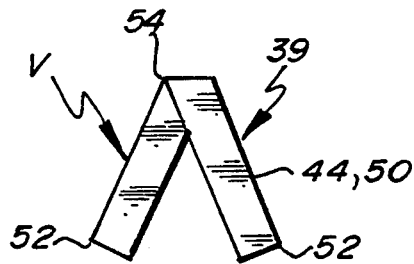
FIG. 6 is a top plan view of the elongate sizing strip folded to a V-shape.
Figure 8:
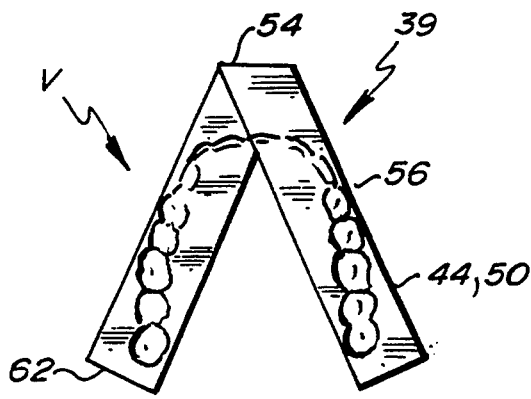
FIG. 8 is a top plan view of the V-shaped sizing strip bearing a dentition imprint.
Figure 7:
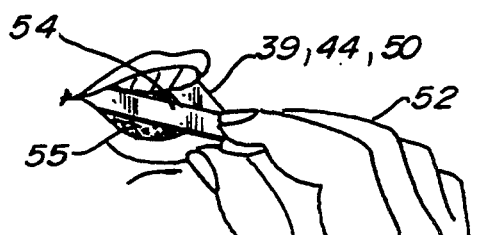
FIG. 7 is a perspective view of the V-shaped sizing strip being placed into a mouth for dentition impression upon the strip.
Figure 9:
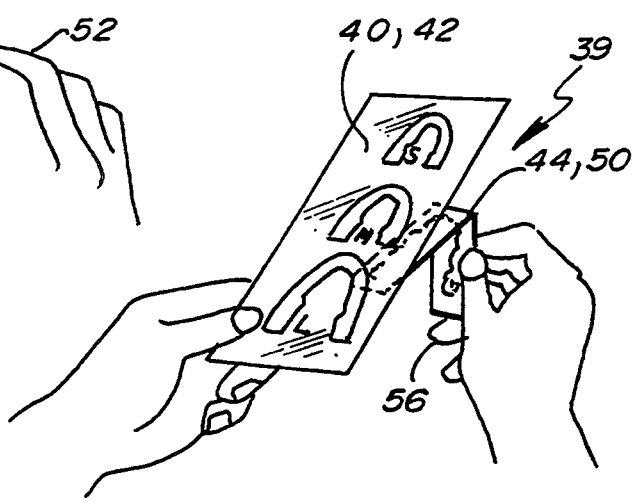
FIG. 9 is a perspective view of the mouthguard sizing kit wherein the sizing strip with its dental imprint is being compared to the sizing chart for selection of the properly sized mouthguard.

Referring to FIGS. 4 through 6, the dentition impression plate 44 suitably may be seen. The plate may take any planar shape. In the preferred embodiment, the impression plate 44 takes the shape of an elongate sizing strip 50. The strip may be of a gum base together with calcium phosphate, flavoring, sodium saccharine and artificial coloring. Alternatively, the strip 50 may be made of a corn syrup based soft candy, such as a licorice, which may further include flour, sugar, corn starch and oil. The strip 50 may also be made of a wax base. The strip 50 may also take the form of nonedible materials capable of receiving impressions such as cardboard, tin foil, styrofoam and paper.

Again referring to FIGS. 4 through 6, the elongate sizing strip 50 has end portions 52 and an intermediate portion 54. The strip 50 generally has a length L equivalent to the circumference C or the complete extension of the dentition 10 as shown in FIG. 1. More specifically but only illustratively, the strip 50 may be approximately 6¼" (15 to 16 centimeters). The strip 50 also has a width W which should be at least as great as the largest molars 20 as shown in FIG. 1. More specifically but again illustratively, the width may generally be 7/16" (1.5 centimeters). To receive an impression, it is important that the sizing strip 50 suitably have some thickness T. Again, more specifically but only illustratively, a thickness T of 3/16" (0.4 centimeters) has been found to be suitable.

Referring to FIGS. 4 through 7, after the sizing strip is removed from packaging, it is generally folded into a V-shape at its intermediate portion 54. Thereafter, the user takes his or her hand 52 and places the V-shaped sizing strip 50 into the mouth 55 afterwhich the lower jaw forces the sizing strip upwardly onto the upper dentition 10 to form a dentition imprint 56 clearly shown in FIG. 8 after the sizing strip 50 is removed from the user's mouth 55. Thereafter, the dentition imprint 56 on the sizing strip 50 is compared to the translucent or semi-transparent sizing chart 42 to assist the user in determining whether they should utilize a Small, Medium or Large mouthguard. Alternatively, the sizing strip 50 may be compared to variously sized actual mouthguards 30.

The present invention may be embodied in other specific forms without departing from the spirit of essential attributes thereof; therefore, the illustrated embodiment should be considered in all respects as illustrative and not restrictive, reference being made to the appended claims rather than to the foregoing description to indicate the scope of the invention.

In the claims:

1. A mouthguard sizing kit for selecting a correctly sized small to large mouthguard for proper fitting over an upper dentition of a mouthguard user's mouth extending from one molar side around bicuspids, canine, incisors, canine and bicuspids and to the other molar side, the kit comprising:
    a) a dentition impression plate for placement into the mouth to receive a dentition imprint when forced against the upper dentition suitably by a lower jaw; and
    b) mouthguard sizing chart with small to large plan views of mouthguards for comparison with the dentition impression for selection of the correctly sized small to large mouthguard for the user.

2. The mouthguard sizing kit of claim 1, wherein the chart is at least semi-transparent.

3. The mouthguard sizing kit of claim 1, wherein the dentition impression plate comprises an elongate sizing strip with a length approximating the upper dentition extension foldable along an intermediate portion to form a V-shape for placement into the mouth.

4. The mouthguard sizing kit of claim 3, wherein the strip is of a width at least as great as approximating large molars.

5. The mouthguard sizing kit of claim 3, wherein the strip is made from a gum base.

6. The mouthguard sizing kit of claim 3, wherein the strip is made of a material from a group comprising gum base, wax base, cardboard, tin foil, styrofoam, paper and corn syrup-based soft candy.

7. A mouthguard sizing kit for selecting a correctly sized small to large mouthguard for proper fitting over an upper dentition of a mouthguard user's mouth extending from one molar side around bicuspids, canine, incisors, canine and bicuspids and to the other molar side, the kit comprising:
    a) a dentition impression plate for placement into the mouth to receive a dentition imprint when forced against the upper dentition suitably by a lower jaw, the plate comprising an elongate sizing strip with a length approximating the upper dentition extension foldable along an intermediate portion to form a V-shape for placement into the mouth; and
    b) mouthguard sizing means which indicates small to large mouthguards for comparison with the dentition impression for selection of the correctly sized small to large mouthguard for the user.

8. The mouthguard sizing kit of claim 7, wherein the mouthguard sizing means comprises a mouthguard sizing chart with top plan views of mouthguards from small to large.

9. The mouthguard sizing kit of claim 8 wherein the chart is at least semi-transparent.

10. The mouthguard sizing kit of claim 7, wherein the strip is of a width at least as great as approximating large molars.

11. The mouthguard sizing kit of claim 7, wherein the strip is made from a gum base.

12. The mouthguard sizing kit of claim 7, wherein the strip is made of a material from a group comprising gum base, wax base, cardboard, tin foil, styrofoam, paper and corn syrup-based soft candy.

13. A mouthguard sizing kit for selecting a correctly sized small to large mouthguard for proper fitting over an upper dentition of a mouthguard user's mouth extending from one molar side around bicuspids, canine, incisors, canine and bicuspids and to the other molar side, the kit comprising:

a) a dentition impression plate for placement into the mouth to receive a dentition imprint when forced against the upper dentition suitably by a lower jaw the plate comprising an elongate sizing strip with a length approximating the upper dentition extension a width at least as great as approximating large molars and being foldable along an intermediate portion to form a V-shape for placement into the mouth and being made from an edible material; and b) mouthguard sizing means which indicates small to large mouthguards for comparison with the dentition impression for selection of the correctly sized small to large mouthguard for the user.

14. The mouthguard sizing kit of claim 13, wherein the mouthguard sizing means comprises a semi-transparent mouthguard sizing chart with top plan views of mouthguards from small to large.

15. The mouthguard sizing kit of claim 13, wherein the mouthguard sizing means comprises mouthguards from small to large.

* * * * *